United States Patent [19]

Walsh et al.

[11] 4,452,809
[45] Jun. 5, 1984

[54] TRANS-4-(2-CHLOROPHENOXY)-1-ETHYL-3-PYRROLIDINOL AND ANTI-DEPRESSANT USE THEREOF

[75] Inventors: David A. Walsh; William J. Welstead, Jr., both of Richmond, Va.

[73] Assignee: A. H. Robins Company, Inc., Richmond, Va.

[21] Appl. No.: 485,497

[22] Filed: Apr. 22, 1983

Related U.S. Application Data

[63] Continuation of Ser. No. 128,691, Mar. 10, 1980, abandoned.

[51] Int. Cl.$^3$ ..................... A61K 31/40; C07D 207/12
[52] U.S. Cl. ...................................... 424/274; 548/541
[58] Field of Search ......................... 424/274; 548/541

[56]     References Cited
U.S. PATENT DOCUMENTS 4,320,137  3/1982  Paoni .................................. 548/541

Primary Examiner—Paul M. Coughlan, Jr.
Assistant Examiner—D. B. Springer

Attorney, Agent, or Firm—George A. Depaoli

[57]     ABSTRACT

Cis and trans-3-aryloxy-4-hydroxypyrrolidines and derivatives thereof having the formula:

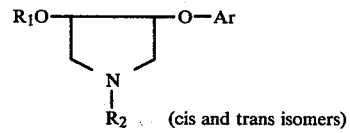

(cis and trans isomers)

are disclosed wherein $R_1$ is hydrogen, loweralkyl, benzyloxycarbonyl and N-loweralkylcarbamoyl; $R_2$ is hydrogen, lower alkyl, cycloalkyl, phenylalkyl, benzyloxycarbonyl, carbamoyl, N-loweralkylcarbamoyl, N-diloweralkylcarbamoyl and parafluorobenzoyl-loweralkyl; Ar is phenyl, substituted phenyl, 1-naphthyl, 2-naphthyl, 1-indenyl and 2-indenyl and pharmaceutically acceptable acid addition and quaternary salts thereof. The compounds have antidepressant, antihypertensive and antiarrythmic activity in animals.

3 Claims, No Drawings

TRANS-4-(2-CHLOROPHENOXY)-1-ETHYL-3-PYRROLIDINOL AND ANTI-DEPRESSANT USE THEREOF

This application is a continuation, of application Ser. No. 128,691, filed Mar. 10, 1980 now abandoned.

BACKGROUND OF THE INVENTION

1. Field of Invention

The present invention relates to certain novel cis and trans isomers of 3-aryloxy-4-hydroxypyrrolidines and derivatives thereof which are useful in treating depression, hypertension or heart arrythmias in animals, with compositions prepared therefrom.

2. Description of the Prior Art

Compounds of the present invention have not been available prior to the present invention. German Offenlegungsschrift No. 2,738,477 has disclosed certain trans-3-aryloxy-4-hydroxypyrrolidines and piperidines which have pertinence to the present invention but which disclosure is subsequent to the present invention. None of the compounds disclosed in that reference are cis isomers. Certain of the compounds of the present invention also differ in having substitution of alkyl, phenylalkyl and cycloalkyl on pyrrolidinyl nitrogen.

SUMMARY OF INVENTION

The present invention provides novel cis and trans isomers of 3-aryloxy-4-hydroxypyrrolidines and derivatives thereof which have important pharmacological activity. The compounds of the invention are represented by the following structure formula:

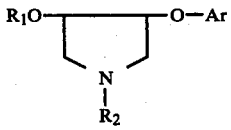

Formula I (cis and trans isomers)

wherein;

$R_1$ represents hydrogen, loweralkyl, benzoyloxycarbonyl, and N-loweralkylcarbamoyl, $R_2$ represents hydrogen, loweralkyl, cycloalkyl, phenylalkyl, benzyloxycarbonyl, carbamoyl, N-loweralkylcarbamoyl, N-di-loweralkylcarbamoyl and parafluorobenzoylloweralkyl, Ar=phenyl, substituted phenyl, 1-naphthyl, 2-naphthyl, 1-indenyl and 2-indenyl, and the pharmaceutically acceptable acid addition and quaternary salts thereof. The compounds have cis or trans configuration.

The compounds of the present invention have antidepressant, hypotensive and cardiovascular activity in animals.

Antidepressant activity was shown to be present by the procedure given by Englehardt, E. L. et al., J. Med. Chem. 11 (2:325 (1968) wherein the novel compounds of the present invention were administered to mice intraperitoneally and the effectiveness of the compounds in blocking the depressant effects which are induced in mice by intravenous administration of 2-oxo-3-isobutyl-9,10, dimethoxy-1,2,3,4,6,7-hexahydro-11bh-benzo[a]quinolizine (tetrabenazine) was determined.

Compounds of the invention for which pronounced antidepressant activity was observed have the formula:

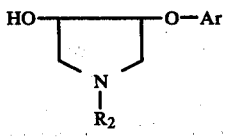

Formula Ia wherein $R_2$ is hydrogen, lower-alkyl or phenylalkyl, and Ar is phenyl or substituted phenyl.

Compounds preferred for their antidepressant activity have the formula:

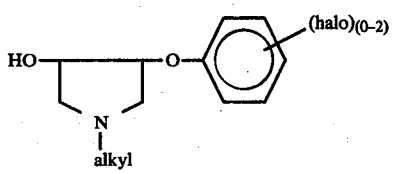

Formula Ib

Illustrative of the antidepressant activity of compounds of Formula Ia are the effective dosages determined by the foregoing anti-tetrabenazine test.

| Compound Example | Antitetrabenazine (Mice) $ED_{50}$ (mg/kg) |
|---|---|
| 3 | 3.7 |
| 46 | 3.5 |
| 49 | 4.8 |
| 48 | 2.8 |

The action of certain compounds disclosed in the present invention in counteracting cardiac arrhythmia is demonstrated by the following procedure. The procedure is carried out under barbiturate anesthesia using adult mongrel dogs of either sex weighing from 8 to 14 kg. A Grass Model 7 polygraph was used for recording femoral arterial blood pressure (Statham P23AC Transducer) and the electrocardiogram (Grass 7P4 Preamplifier). Ouabian was given intravenously in an initial dose of 40γ/kg in a second dose of 20γ/kg, given 30 minutes after the first dose, and in subsequent doses of 10γ/kg which were repeated at 15 minute intervals as required for producing cardiac arrhythmias that persisted for at least 15 minutes. When the arrhythmias were established the test compounds were administered by infusion (Harvard Model 942 Infusion Pump) into a femoral vein at a rate of 1 mg/kg/min. Concentrations of compounds were adjusted according to the weight of the dog to allow a volume infusion of 1 ml/min. Compounds that are considered to be active as antiarrhythmic agents cause reversion to sinus rhythm which is maintained for at least 60 minutes.

Compounds of the invention for which pronounced antiarrhythmic activity was observed have the formula:

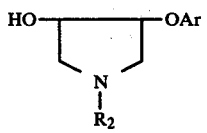

Formula Ic wherein $R_2$ is hydrogen and lower alkyl, and Ar is 1 and 2-naphthyl and 4 and 5-indenyl.

The compound of Example 55 represents a preferred compound exhibiting exceptional antharrhythmic activity at a minimum effective dose of 10.7 mg/kg using the foregoing procedure.

It is accordingly an object of the present invention to provide cis and trans-3-aryloxy-4-hydroxypyrrolidines and derivatives thereof and methods of making same, which have a high degree of antidepressant activity.

Another object is to provide cis and trans-3-aryloxy-4-hydroxypyrrolidines and derivatives thereof which have antiarrhythmic and anti-hypertensive activities in animals.

A still further object is to provide methods of using the cis and trans-3-aryloxy-4-hydroxypyrrolidines as antidepressants, hypotensive agents and antiarrythmic agents in the treatment of living animals, especially mammalian subjects in need of treatment. Additional objects will be apparent to one skilled in the art and still other objects will become apparent hereinafter.

DETAILED DESCRIPTION OF THE INVENTION

The present invention encompasses the novel cis and trans isomers of 3-aryloxy-4-hydroxypyrrolidines and derivatives thereof as set forth hereinabove in Formula I and the definitions therewith as composition of matter and the utilization of these novel compounds in living animals for their pharmacological effect as set forth hereinabove and below.

The term "loweralkyl" as used in the specification and claims includes straight and branched chain radicals of up to eight carbon atoms inclusive and is exemplified by such groups as methyl, ethyl, propyl, isopropyl, butyl isobutyl, tertiary butyl, amyl, isoamyl, hexyl, heptyl, octyl and the like.

The term "substituted phenyl" as used in the specification and claims includes phenyl substituted in one to 3 positions by one or more radicals selected from halogen, O-loweralkyl, —NHC(O)CH$_3$, CF$_3$, —C(O)CH$_3$, —CH$_2$CH=CH$_2$, alkyl, hydroxy, —OCH$_2$phenyl, and —C(O)NH$_2$.

By "cycloalkyl" is meant cycloalkyl radicals having 1 to 9 carbon atoms and includes such radicals as cyclopropyl, cyclobutyl, cyclopentyl, cyclohexyl and the like.

Representative of phenylalkyl radicals are benzyl (phenylmethyl), α-methylbenzyl, phenylethyl, phenylpropyl, phenylbutyl and the like.

The starting materials used in preparing the novel trans isomer compounds of Formula I are 1-phenylalkyl-3,4-epoxypyrrolidines such as 1-benzyl-3,4-epoxypyrrolidine; 1-alkyl-3,4-epoxypyrrolidines such as 1-ethyl-3,4-epoxypyrrolidine; and 1-cycloalkyl-3,4-epoxypyrrolidines such as 1-cyclohexyl-3,4-epoxypyrrolidine.

Preparation of these 1-substituted epoxypyrrolidines is represented by the following equation:

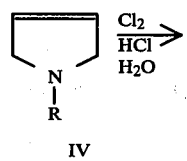

IV

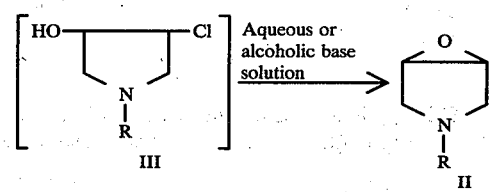

wherein R is loweralkyl, phenylalkyl or cycloalkyl. Generally, the chlorination step is accomplished in 2-6 hrs and the intermediate III need not be isolated. Crude epoxypyrrolidines are obtained by solvent extraction and converted to crystalline salt such as oxalates. Pure free base of the epoxypyrrolidines may be obtained from the oxalate salt by partitioning between 5% aqueous sodium carbonate and methylene chloride and thereafter drying over anhydrous sodium sulfate and evaporating the methylene chloride. The pyrrolines used in these starting preparations are prepared according to the procedure of U.S. Pat. No. 3,691,198 and the procedure for the preparation of 1-cyclohexyl-Δ$^3$-pyrroline is given in Preparation 1.

Preparation of the epoxypyrrolidines used to prepare the trans isomers of Formula I are given in Preparations 2-4.

The starting materials used in preparing the cis isomers of compounds of Formula I was cis-benzyl-3,4-pyrrolidinediol as given in Preparation 5. Cis-3,4-pyrrolidinediols were first prepared by A. J. Hill et al., J. Amer. Chem. Soc. 76, 3548 (1954).

Preparation 1

1-Cyclohexyl-Δ$^3$-pyrroline

A solution of 5.19 kg (52.3 moles) of cyclohexylamine in 4.0 liters of benzene was heated to mild reflux (92° C.) and then the heating discontinued. To the solution was added, dropwise, 1,635 g (13.1 moles) of 1,4-dichlorobutane at a rate sufficient to maintain gentle reflux, 3 hours time being required. Heating was continued and the reactants were heated at reflux temperature for 18 hours. The mixture was cooled to about 50° C. and filtered to remove the hydrochloride salt. Carbon dioxide was bubbled into the filtrate to precipitate excess amine carbonate salt which was removed by filtration. Solvent was removed from the filtrate by distillation under reduced pressure and the reddish fluid residue slightly contaminated with benzene weighed 1,506 g. (76% yield).

Preparation 2

1-Benzyl-3,4-epoxypyrrolidine Oxalate

A mixture of 31.8 g. (0.20 mole) of N-benzyl-Δ$^3$-pyrroline, 25 l. of concentrated hydrochloric acid and 300 ml. of water was treated with a stream of chlorine gas for 2 hr. The solution was filtered and the filtrate was made basic with 20% sodium hydroxide. The basic solution was extracted with three 150 ml. portions of methylene chloride. The combined methylene chloride extracts were dried over magnesium sulfate and evaporated to give 48.5 g. of crude chlorohydrin as a dark oil. This oil was stirred with 200 ml. of 20% sodium hydroxide 0.5 hr., 700 l. of water was added, and the base was extracted with four 100-ml portions of methylene chloride. The combined methylene chloride extracts were dried over magnesium sulfate and concentrated to yield 34.9 g. (99%) of crude epoxide as a dark oil. The oxalate salt was prepared in 81% yield. Recrystallization from 95% ethanol gave the salt as off-white needles, m.p. 148°–49°/d.

Analysis: Calculated for $C_{13}H_{15}NO_5$: C, 58.86; H, 5.70; N, 5.28. Found: C, 58.55; H, 5.68; N, 5.25.

Preparation 3

1-Ethyl-3,4-epoxy-pyrrolidine Oxalate

A mixture of 61 g. (0.63 mole) of 1-ethylpyrroline, 50 ml. of concentrated aqueous hydrochloric acid and 600 ml. of water was treated with chlorine gas for 2.5 hr. The mixture was filtered through cotton and the filtrate was washed with two 100-ml. portions of methylene chloride. The aqueous layer was made basic with 20% sodium hydroxide, heated on a steam bath for 0.5 hr. and extracted with three 100-ml. portions of methylene chloride. The combined extracts were dried over anhydrous sodium sulfate and concentrated and the residue vacuum distilled to give 39.4 g. (56%) of the epoxide as a clear oil (b.p. 75°–90° @ 28 mm). The epoxide was converted to the oxalate and the salt was recrystallized from absolute ethanol to give white needles, m.p. 142°–4°d.

Analysis: Calculated for $C_8H_{13}NO_5$: C, 47.29; H, 6.45; N, 6.89. Found: C, 47.12; H, 6.42; N, 6.82.

Preparation 4

1-Cyclohexyl-3,4-epoxypyrrolidine Oxalate

A solution of 151.3 g. (1.0 mole) of N-cyclohexyl-$\Delta^3$-pyrrolidine, 100 ml of concentrated hydrochloric acid and 1.8 liters of water was treated with a stream of chlorine gas until uptake ceased ($\sim$6 hrs). The solution was washed with methylene chloride and the acidic solution was left standing overnight. The solution was then made basic with 50% sodium hydroxide and extracted with methylene chloride. The combined extracts were concentrated to give 185 g of chlorohydrin as residue. The residue was slowly poured into an ethanol solution containing 20% sodium hydroxide. The mixture was stirred for 0.5 hr and then 3.5 liters of water was added. The mixture was extracted with methylene chloride and the combined extracts were dried over anhydrous sodium sulfate and concentrated to give 154 g. (92%) of amine epoxide. An NMR analysis indicates this residue is 86% epoxide and 14% 3,4-dichloro-N-cyclohexylpyrrolidine. The residue was vacuum distilled to give the epoxide as a water-white liquid, b.p. 71° C. at 0.6 mm. A portion of the liquid was converted to the oxalate to give a white solid, m.p. 155°–6°d when recrystallized from ethanol.

Analysis: Calculated for $C_{12}H_{19}NO_5$: C, 56.02; H, 7.44; N, 5.44. Found: C, 56.05; H, 7.50; N, 5.34.

Preparation 5

1-Phenylmethyl-3,4-pyrrolidinediol Monohydrochloride cis Isomer

A mixture of 80 g. (0.32 mole) of meso-1,4-dibromo-2,3-dihydroxybutane, 34 g. (0.32 mole) of benzylamine, 3 g. of potassium iodide and 140 g. (1.0 mole) of potassium carbonate in 250 ml of 95 ethanol was heated at reflux for 18 hr., then cooled and filtered. The filtrate was concentrated and the residue was washed with several portions of boiling ethyl acetate. The extracts were combined, washed with a small amount of water, dried over anhydrous sodium sulfate and concentrated to give 30 g residue representing a 48% yield of 1-phenylmethyl-3,4-pyrrolidinediol cis isomer. A portion was converted to the hydrochloride salt with hydrogen chloride in isopropyl alcohol and recrystallized from isopropyl alcohol as off-white granules, m.p. 115.0°–116.5°.

Analysis: Calculated for $C_{11}H_{16}ClNO_2$: C, 57.52; H, 7.02; N, 6.10. Found: C, 57.16; H, 6.91; N, 6.01.

Synthesis of trans-isomer compounds of Formula I which are part of the present invention and which also serve as reactants for the preparation of other compounds of the invention was started by reacting aryloxy compounds with appropriately 1-substituted-3,4-epoxypyrrolidines as exemplified by the following equation:

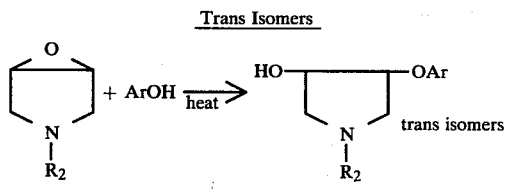

wherein $R_2$ is phenylalkyl, alkyl and cycloalkyl, and Ar is as defined hereinabove.

Synthesis of cis isomers which are part of the present invention and which serve as reactants for other compounds of the invention was started by reacting 1-benzyl-3,4-pyrrolidinediol cis isomer with Ar-F compounds according to the following formula:

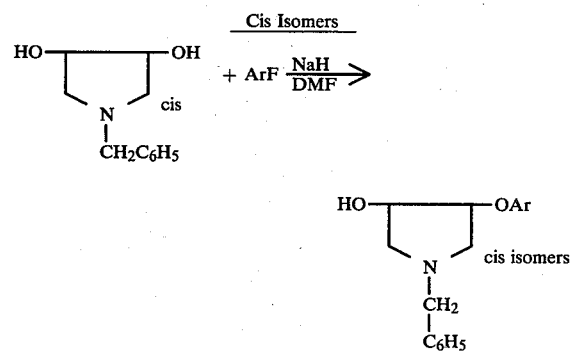

wherein Ar is as defined hereinabove.

In preparing compounds having further variation under Formula I, the following methods may be used for preparation of either trans or cis isomers.

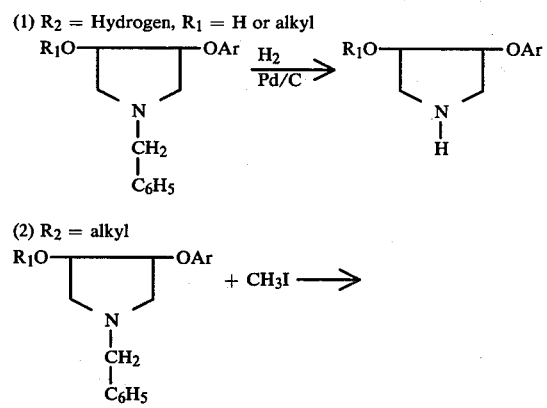

7
-continued
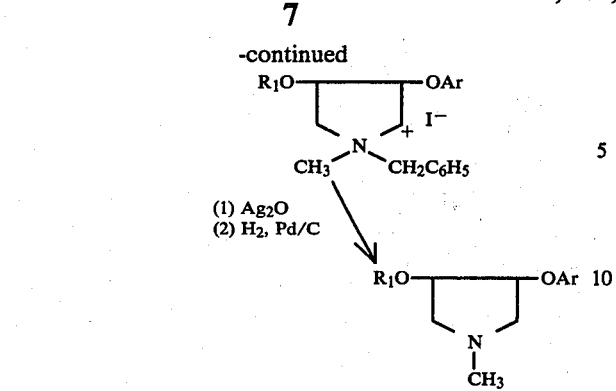
(1) Ag₂O
(2) H₂, Pd/C
(3) R₁ = alkyl
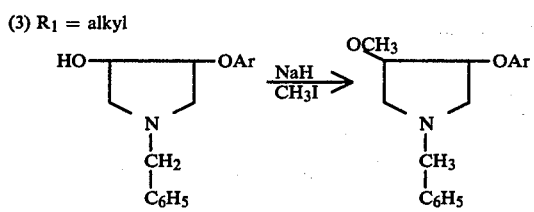
(4) R₂ = (CH₂)₂—C(=O)—C₆H₄—F
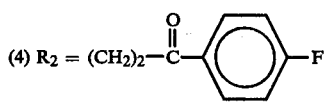
+
(CH₃)₂N—CH₂—CH₂—C(=O)—C₆H₄—F
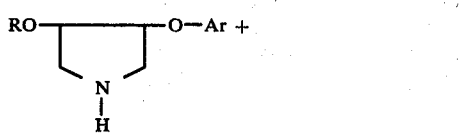
(5)
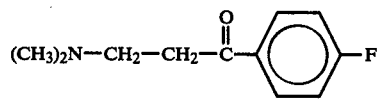
+ Benzylchloroformate →
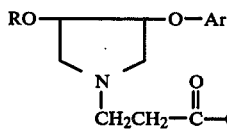
+
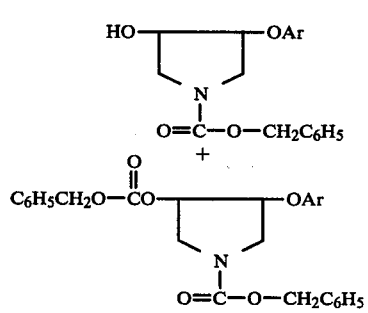
8
-continued
Ar = phenyl substituted with halide;
R₂ = H
HBr ↓
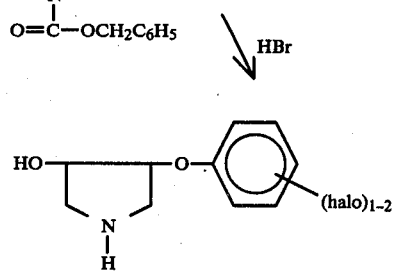
(7) R₂ = —C(=O)—NH₂
 + Nitrourea →
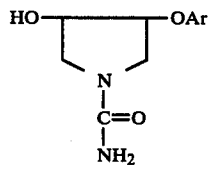
(8) R₂ = —C(=O)—N(CH₃)₂
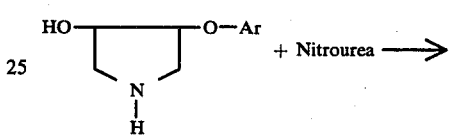 dimethyl carbamyl chloride →
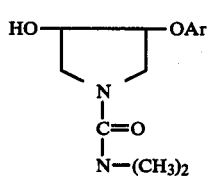
(9) R₂ = —C(=O)—NH—alkyl
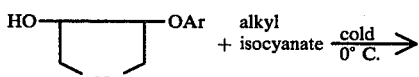 alkyl isocyanate, cold 0° C. →
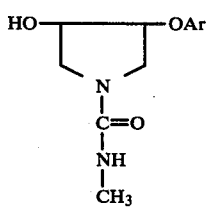

-continued

(10) $R_1 = CH_3NHC(=O)-O$; $R_2 = -C(=O)-N(CH_3)_2$

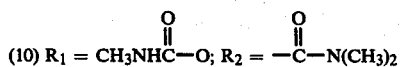

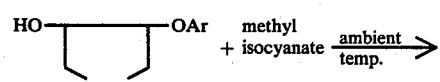

(11) $R_1 = H$; $Ar = C_6H_5$ starting from $Ar = C_6H_4$—halo

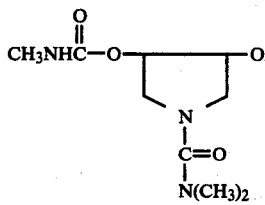

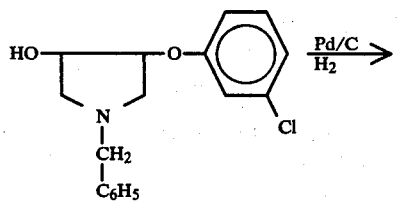

To obtain the free base of a compound prepared as a salt, the salt is partitioned between methylene chloride and 5% sodium hydroxide. The methylene chloride layer is dried over sodium sulfate and concentrated to give the base as residue.

The novel compounds of the present invention and the methods for their preparation are exemplified more fully by the following illustrative examples, the scope of the invention is, however, not limited thereto. As will be readily identifiable from a consideration of the examples and the foregoing outline, many of the compounds under the scope of Formula I may be also considered as intermediates in the synthesis of other compounds of Formula I.

EXAMPLE 1

Trans-4-phenoxy-1-phenylmethyl-3-pyrrolidinol

A mixture of 12.3 g. of 1-benzyl-3,4-epoxypyrrolidine, 13.2 g. of phenol and 3 drops of water was heated at 120° C. under nitrogen gas for 20 hr. The mixture was cooled and dissolved in 100 ml. ethyl ether. The ethereal solution was extracted with 2×50 ml. of 5% sodium hydroxide and then washed with water. After being dried with anhydrous sodium sulfate, the solvent was evaporated and the residue weighed 14.3 g. Two crystallizations from cyclohexane gave analytically pure product melting at 101°-104° C. The yield was 24% of theory.

Analysis: Calculated for $C_{17}H_{19}NO_2$: C, 75.81; H, 7.11; N, 5.20. Found: C, 75.71; H, 7.10; H, 5.38.

EXAMPLE 2

Trans-3-hydroxy-1-methyl-4-phenoxy-1-phenylmethyl-pyrrolidinium Iodide

A solution of 8.0 g. (56 mmol) of methyl iodide in 30 ml of dry ethyl ether was added dropwise to a stirred solution of 7.0 g. (26 mmol) of trans-4-phenoxy-1-phenylmethyl-3-pyrrolidinol in 70 ml. of dry diethyl ether. The mixture was stirred for two days and then concentrated under reduced pressure. The 10.7 g. of crystalline residue was washed with tetrahydrofuran and dried, and gave 10.4 g. (97%) of white powder, m.p. 122°-27° C.

Analysis: Calculated for $C_{18}H_{22}INO_2$: C, 52.57; H, 5.39; N, 3.41. Found: C, 52.78; H, 5.45; N, 3.55.

EXAMPLE 3

Trans-1-methyl-4-phenoxy-3-pyrrolidinol

A solution of 9.3 g. (22.6 mmol) of trans-3-hydroxy-1-methyl-4-phenoxy-1-phenylmethylpyrrolidinium iodide in 200 ml. of absolute ethanol and 100 ml. of 190 ethanol was stirred at ambient temperature for 0.5 hr. with 2.6 g. (11.3 mmol) of silver oxide. After 0.2 g. more silver oxide was added, the mixture was warmed to 45° C. and stirred for an additional 15 min. The mixture was separated by filtration through Celite, and the volume of the filtrate was reduced to 200 ml. This solution was treated with ca. 0.5 g. of 10% Pd/C catalyst and was shaken with $H_2$ in the Parr reduction apparatus for 3 hr. The suspension was filtered through Celite and the filtrate was concentrated to give 4.3 g. of crystalline solid. This material, when recrystallized from cyclohexane, gave 3.66 g. (84%) of off-white crystals, m.p. 89.0°-90.0° C.

Analysis: Calculated for $C_{11}H_{15}NO_2$: C, 68.37; H, 7.82; N, 7.25. Found: C, 68.11; H, 7.83; N, 7.22.

EXAMPLE 4

Trans-3-methoxy-4-phenoxy-1-phenylmethylpyrrolidine Oxalate 8.1 g. (0.03 mole) of trans-4-phenoxy-1-phenylmethyl-3-pyrrolidinol was mixed with 0.72 g (0.03 mole) of sodium hydride (1.3 g of 55% in oil, washed with 3×10 ml diethyl ether) in 50 ml. of dimethylformamide and stirred until hydrogen evolution ceased. 4.3 g (0.03 mole) of methyl iodide was added and the mixture was stirred for 18 hr. The reaction was worked up by pouring into 400 ml of water and extracting with 3×100 ml of diethyl ether. The diethyl ether was evaporated, leaving 7.9 g of residue. Addition of petroleum ether caused precipitation of starting material, which was removed by filtration. The residue after evaporation of the mother liquor was chromatographed on silica gel eluting the product with 10% acetone in benzene. The yield of pure product my NMR was 5.0 g. (59%). A small amount was converted to the oxalate in iso-PrOH and recrystallized from i-PrOH; m.p. 122°-25° C.

Analysis: Calculated for $C_{20}H_{23}NO_6$: C, 64.33; H, 6.21; N, 3.75. Found: C, 63.93; H, 6.21; N, 3.69.

EXAMPLE 5

Trans-3-methoxy-4-phenoxypyrrolidine Fumarate

A solution of 4.2 g. (0.015 mole) of 3-methoxy-4-phenoxy-1-phenylmethylpyrrolidine in 70 ml. of ethanol was treated with ca 0.2 g of Pd/C catalyst and shaken under hydrogen at 60° C. in the Parr apparatus for 3 hr. After cooling, the mixture was filtered and the solvent was evaporated. The 2.9 g (100%) of crude product (good purity by NMR) was converted to the fumarate in isopropyl alcohol. The pale yellow precipitate melted at 134°–136° C.

Analysis: Calculated for $C_{15}H_{19}NO_6$: C, 58.25; H, 6.19; N, 4.53. Found: C, 58.15; H, 6.27; N, 4.46.

EXAMPLE 6

Trans-4-phenoxy-3-pyrrolidinol Fumarate

A solution of 14.8 g. of 1-benzyl-4-phenoxy-3-pyrrolidinol in 200 ml. of ethanol was treated with ca. 3 g. of 10% palladium-on-charcoal catalyst and was shaken with hydrogen at 60° C. in the Parr reduction apparatus for 5 hr. The suspension was cooled, filtered and the solvent evaporated at reduced pressure. The residue was converted to the fumarate using isopropyl alcohol. The yield of product, m.p. 158°–62° C. was 14.1 g (87%).

Analysis: Calculated for $C_{14}H_{17}NO_6$: C, 56.95; H, 5.80; N, 4.74. Found: C, 56.91; H, 5.97; N, 4.78.

EXAMPLE 7

Trans-1-(4-fluorophenyl)-3-(3-hydroxy-4-phenoxy-1-pyrrolidinyl)-1-propanone

A mixture of 3.6 g. (0.02 mole) of 4-phenoxy-3-pyrrolidinol, 5 g. (0.0215 mole) of β-dimethylamino-p-fluoropropiophenone hydrochloride, 10 g. of potassium carbonate and 50 ml. of dimethylformamide was heated with stirring at 70° C. for 6 hr. while nitrogen gas was bubbled through the reaction mixture. The mixture was poured into water and extracted twice with benzene. The combined extracts were dried over anhydrous sodium sulfate and concentrated to give 6.1 g. of an oil as residue. The oil was chromatographed on 130 g. of silica gel. The desired compound was eluted with 20% acetone in benzene and 2.6 g. (39%) of an oil which gradually crystallized upon standing was obtained. This solid was recrystallized from petroleum ether diethylether to yield a white solid, m.p. 77°–80° C.

Analysis: Calculated for $C_{19}H_{20}FNO_3$: C, 69.28; H, 6.12; N, 4.25. Found: C, 69.43; H, 6.23; N, 4.18.

EXAMPLE 8

Trans-4-(4-chlorophenoxy)-1-phenylmethyl-3-pyrrolidinol

A mixture of 12.3 g. of 1-benzyl-3,4-epoxypyrrolidine, 18.0 g. of p-chlorophenol and 3 drops of water was heated at 120° C. under nitrogen gas for 20 hr. The mixture was cooled and dissolved in 100 ml. diethyl ether. The ethereal solution was extracted with 2×50 ml. 5% sodium hydroxide and then washed with water. After being dried with anhydrous sodium sulfate, the solvent was evaporated and the residue weighed 14.3 g. Two crystallizations from cyclohexane gave 4.7 g (29%) of analytically pure product which melted at 101°–104° C.

Analysis: Calculated for $C_{17}H_{18}ClNO_2$: C, 67.21; H, 5.97; N, 4.61. Found: C, 67.35; H, 6.10; N, 4.69.

EXAMPLE 9

Trans-3-(4-chlorophenoxy-4-{phenylmethyl[carbonylbis(oxy)]}-1-pyrrolidine carboxylic acid phenylmethyl ester A solution of 14.0 g. (0.046 mole) of trans-4-(4-chlorophenoxy)-1-phenylmethyl-3-pyrrolidinol and 5 g. (0.05 mole) of triethylamine in 200 ml. of benzene was added dropwise to a cold (15° C.) solution of 30.0 g. (0.175 mole) of benzylchloroformate in 100 ml. of benzene. The mixture was allowed to warm to room temperature and stirred over night. The precipitate was removed by filtration and discarded and the filtrate was concentrated and the residue heated under high vacuum to remove excess reactants and by-products. The resulting gum was chromatographed on silica gel, eluting the desired product with 20% acetone in benzene. 5 g. of product was obtained after evaporation.

EXAMPLE 10

Trans-4-(4-chlorophenoxy)-3-pyrrolidinol Hydrobromide

A solution of 5 g. of 3-(4-chlorophenoxy)-4-{phenylmethyl[carbonylbis(oxy)]}-1-pyrrolidinecarboxylic acid phenylmethyl ester trans isomer in 30 ml. of ethanol and 50 ml. of 48% hydrogen bromide was heated at 115° C. for 16 hrs. and then cooled and diluted with 100 ml. water. The solution was extracted with 2×50 ml. of methylene chloride and the aqueous layer was evaporated to dryness. The powder that remained was the product in 82% yield with a melting point of 190°–92° C.

Analysis: Calculated for $C_{10}H_{13}NO_2BrCl$: C, 40.77; H, 4.45; N, 4.76. Found: C, 41.01; H, 4.46; N, 4.85.

EXAMPLE 11

Trans-3-(4-chlorophenoxy)-4-hydroxy-1-pyrrolidinecarboxamide

A solution of 4.4 g. of 4-(chlorophenoxy)-3-pyrrolidinol and 2.8 g. of nitrourea in 100 ml. of 90% ethanol was heated at 50° C. for 20 hr. Some of the solvent was removed under vacuum and the remaining slurry was diluted with 50 ml. water. The precipitate was filtered, triturated with acetone, filtered and dried. Yield 1.8 g., m.p. 223°–225° C.

Analysis: Calculated for $C_{11}H_{13}N_2O_3Cl$: C, 51.47; H, 5.11; N, 10.91. Found: C, 51.18; H, 5.02; N, 10.88.

EXAMPLE 12

Trans-3-(4-chlorophenoxy)-4-hydroxy-N,N-dimethyl-1-pyrrolidinecarboxamide

A solution of 3.5 g. of 4-(4-chlorophenoxy)-3-pyrrolidinol, 1.8 g. of dimethylcarbamyl chloride and 1.7 g. of triethylamine in 300 ml of methylene chloride was stirred for 60 hr. The solvent was removed under vacuum, 300 ml of benzene was added and the mixture was refluxed for 2 hr., then filtered. After solvent evaporation, the residue was dissolved in cyclohexane-benzene and charcoaled. The product was then crystallized, collected by filtration and recrystallized from cyclohexane-benzene; m.p. 137°–142° C. Analysis: Calculated for $C_{13}H_{17}N_2O_3Cl$: C, 54.84; H, 6.02; N, 9.84. Found: C, 54.64; H, 6.01; N, 9.77.

EXAMPLE 13

Trans-3-(4-chlorophenoxy)-4-hydroxy-N-methyl-1-pyrrolidinecarboxamide Hemihydrate A solution of 0.9 g. of 4-(4-chlorophenoxy)-3-pyrrolidinol in 50 ml. of methylene chloride was cooled to 0° C. and 0.24 g. of methyl isocyanate in 5 ml. of methylene chloride was added dropwise over the period of 10 min. Cooling was discontinued and stirring was continued for 1 hr. Solvent was then removed and the residue was crystallized from dimethylsulfoxide-water; m.p. 95 0°–98.5° C.

Analysis: Calculated for $C_{12}H_{15}N_2O_3Cl$: C, 51.53; H, 5.77 N, 10.02. Found: C, 51.64; H, 5.79; N, 10.09.

EXAMPLE 14

Trans-3-{[(methylamino)carbonyl]oxy}-4-(4-chlorophenoxy)-N,N-dimethyl-1-pyrrolidinecarboxamide A solution of 1.0 g. (0.003 mole) of trans-3-(4-chlorophenoxy)-4-hydroxy-N,N-dimethyl-1-pyrrolidinecarboxamide and 1.0 g. (0.02 mole) of methylisocyanate in 20 ml. of methylene chloride was let stand at ambient temperature for 48 hr. The solution was concentrated to give an oil which crystallized upon standing. The solid was recrystallized from benzene-cyclohexane to yield 0.6 g. (50%) of white solid, m.p. 132°–134° C.

Analysis: Calculated for $C_{15}H_{20}ClN_3O_4$: C, 52.71; H, 5.90; N, 12.29. Found: C, 53.09; H, 5.96; N, 12.28.

EXAMPLE 15

Trans-4-(2,6-dichlorophenoxy)-1-phenylmethyl-3-pyrrolidinol

A mixture of 35.0 g. of 1-benzyl-3,4-epoxypyrrolidine and 32.6 g. of 2,6-dichlorophenol was heated at 125° C. for 3 hr. The mixture was cooled, dissolved in methylene chloride and extracted with dilute sodium hydroxide. The residue after the solvent was evaporated was purified by column chromatography. The product was eluted with 30% ethyl acetate in benzene and crystallized from cyclohexane. Yield was 43 g (64%) m.p. 78°–80° C.

Analysis: Calculated for $C_{17}H_{17}NO_2Cl_2$: C, 60.37; H, 5.07; N, 4.14. Found: C, 60.42; H, 5.06; N, 4.12.

EXAMPLE 16

Trans-3-(2,6-dichlorophenoxy)-4-{phenylmethyl[carbonylbis(oxy)]}-1-pyrrolidinecarboxylic Acid Phenylmethyl Ester To a solution of 3.4 g. of trans-1-benzyl-4(2,6-dichlorophenoxy)-3-pyrrolidinol and 1.05 g. of triethylamine in 25 ml. of benzene was added dropwise a solution of 4.0 g. of benzylchloroformate in 20 ml. of benzene. The mixture was stirred for 30 min. after addition was complete; then filtered and the solvent was evaporated under reduced pressure. The residue was dissolved in 50 ml. methylene chloride and 6.0 g. of benzylchloroformate was added. The mixture was stirred overnight; then the solvent was evaporated and the residue chromatographed on silica gel. The product was eluted with 20% ethyl acetate in benzene and then stirred with petroleum ether until it crystallized. The white crystals weighed 4.7 g. (90%) and melted at 93°–95° C.

Analysis: Calculated for $C_{26}H_{23}NO_6Cl_2$: C, 60.48; H, 4.49; N, 2.71. Found: C, 60.61; H, 4.55 N, 2.76.

EXAMPLE 17

Trans-4-(2,6-dichlorophenoxy)-3-pyrrolidinol Hydrobromide

A solution of 12.2 g. 3-(2,6-dichlorophenoxy)-4-[phenylmethyl(carbonylbis(oxy))]-1-pyrrolidinecarboxylic acid phenylmethyl ester trans isomer in 120 ml. of ethanol and 140 ml. of 48% hydrogen bromide was stirred at 125° C. for 16 hr. and then cooled and diluted with 300 ml. water. The solution was then extracted with 2×100 ml. methylene chloride and the aqueous layer was evaporated to dryness. Trituration with 30% diethylether in isopropyl alcohol gave 7.4 g. (95%) of white crystalline hydrobromide; m.p. 192°–5° C.

Analysis: Calculated for $C_{10}H_{12}NO_2BrCl_2$: C, 36.51; H, 3.68; N, 4.26. Found: C, 36.49; H, 3.72; N, 4.36.

EXAMPLE 18

Trans-4-(2,3-dichlorophenoxy)-1-phenylmethyl-3-pyrrolidinol Hydrochloride

A mixture of 21.5 g. (0.12 mole) of 1-benzyl-3,4-epoxypyrrolidine, 27.8 g. (0.17 mole) of 2,3-dichlorophenol and 2 drops of concentrated hydrochloric acid was heated at 120° C. overnight. The dark mixture was dissolved in methylene chloride and washed with four 100-ml portions of 5% sodium hydroxide and once with water. The methylene chloride layer was dried over anhydrous sodium sulfate-potassium hydroxide and concentrated to give 35.8 g of dark gum as residue. This gum was chromatographed on 800 g. of silica gel and the product was eluted with an acetone-benzene solution. The appropriate fractions were concentrated to give 25 g. (60%) of an oil. A portion of this oil was converted to the hydrochloride to yield white solid, m.p. 219°–22° C.

Analysis: Calculated for $C_{17}H_{18}Cl_3NO_2$: C, 54.50; H, 4.84; N, 3.74. Found: C, 54.53; H, 4.82; N, 3.53.

EXAMPLE 19

Trans-4-(2,3-dichlorophenoxy)-1-[(phenylmethoxy)carbonyl]-3-pyrrolidinol

A mixture of 8.5 g (0.023 mole) of trans-4-(2,3-dichlorophenoxy)-1-phenylmethyl-3-pyrrolidinol hydrochloride and 100 liters of methyl chloride was cooled and treated dropwise with a solution of 23 g (0.125 mole) of benzylchloroformate in 100 ml of methylene chloride. The mixture was stirred at ambient temperature for 48 hr and then washed successively with water, 2 N hydrochloric acid, 5% sodium hydroxide and water. The methylene chloride layer was dried over anhydrous sodium sulfate and then subjected to vacuum distillation at 100°/1.0 mm. to remove the methylene chloride, excess benzylchloroformate and benzyl chloride. An NMR analysis of the pot residue indicated only the oxygen was substituted. An additional 25 ml. of benzylchloroformate and 100 ml. of methylene chloride was added to the residue and the solution stirred at ambient temperature for 48 hr. The mixture was purified as above to give 14.6 g. of residue which was chromatographed on 300 g. of silica gel. The chromatography gave 5.6 g. of the disubstituted compound (See Example 20) and 1.0 g. of the titled compound as a white solid, m.p. 130°–2° C. (recrystallized from benzene).

Analysis: Calculated for $C_{16}H_{17}Cl_2NO_4$: C, 56.56; H, 4.48; N, 3.67. Found: C, 56.80; H, 4.48; N, 3.67.

EXAMPLE 20

Trans-3-(2-dichlorophenoxy)-4-{phenylmethyl[carbonylbis(oxy)]}-1-pyrrolidine carboxylic acid phenylmethylester This disubstituted compound resulted from chromatography separation in amount of 5–6 g. in Example 19.

EXAMPLE 21

Trans-4-(2,3-dichlorophenoxy)-3-pyrrolidinol Hydrobromide

A mixture of 5.6 g. (0.011 mole) of 3-(2-dichlorophenoxy)-4-{phenylmethyl[carbonylbis(oxy)]}-1-pyrrolidine carboxylic acid phenylmethylester trans isomer, 60 ml. of ethanol and 70 ml. of 48% aqueous hydrogen bromide was heated at 125° C. overnight. The mixture was poured into 150 ml. of water and extracted three times with methylene chloride. The aqueous solution was concentrated to give an oily residue which crystallized upon standing. The solid was washed with isopropyl alcohol-diethylether, collected by filtration and recrystallized from isopropyl alcoholdiethylether to yield 1.5 g. (45%) of a pink solid, m.p. 134°-8° C.

Analysis: Calculated for $C_{10}H_{12}BrCl_2NO_2$: C, 36.51; H, 3.68; N, 4.26. Found: C, 36.54; H, 3.69; N, 4.32.

EXAMPLE 22

Trans-1-benzyl-4-(3-methylphenoxy)-3-pyrrolidinol Hydrochloride

A mixture of 17.5 g. of 1-benzyl-3,4-epoxypyrrolidine and 20 g. of m-cresol was heated at 115° C. for 18 hr. under nitrogen gas. After cooling, the mixture was dissolved in benzene and washed with 5% sodium hydroxide to remove excess cresol. Stirring with 50 g. of silica gel removed much of the colored material. The solution was reduced in volume and some of the residue was converted to the hydrochloride. This salt was recrystallized from isopropyl alcohol-diethyl ether and melted at 163°-165° C.

Analysis: Calculated for $C_{18}H_{22}NO_2Cl$: C, 67.60; H, 6.93; N, 4.38. Found: C, 67.39; H, 6.97; N, 4.43.

EXAMPLE 23

Trans-4-(3-methylphenoxy)-3-pyrrolidinol Oxalate

A solution of 8.2 g. of 1-benzyl-4-(3-methylphenoxy)-3-pyrrolidinol in 150 ml. of ethanol was treated with ca. 0.5 g. of 10% palladium-on-charcoal catalyst and was shaken with hydrogen at 60° C. in the Parr apparatus for 2 hr. The suspension was cooled, filtered and the solvent evaporated under vacuum. The base was converted to the oxalate in isopropyl alcohol, filtered and dried. The salt was obtained in 86% yield and melted at 150°-155° C.

Analysis: Calculated for $C_{13}H_{17}NO_5$: C, 55.12; H, 6.05; N, 4.94. Found: C, 54.75; H, 6.07; N, 5.06.

EXAMPLE 24

Trans-4-(2,3-dimethylphenoxy)-1-phenylmethyl-3-pyrrolidinol

A mixture of 17.5 g. (0.10 mole) of 1-benzyl-3,4-epoxypyrrolidine, 18.3 g. (0.15 mole) of 2,3-dimethylphenol and 2 drops of concentrated hydrochloric acid was heated at 120° C. under a nitrogen atmosphere overnight. The reaction mixture was dissolved in methylene chloride and washed with four 100-ml portions of 5% sodium hydroxide and once with water. The methylene chloride layer was dried over anhydrous sodium sulfate-potassium hydroxide and concentrated to give 28.6 g. of dark oil as residue. This oil was chromatographed on 600 g. of silica gel and the product was eluted with an acetone-benzene solution. The appropriate fractions were concentrated to give an oil which crystallized upon standing. This solid was recrystallized from ligroin to give 9.1 g. (31%) of white solid, m.p. 100°-4° C.

Analysis: Calculated for $C_{19}H_{23}NO_2$: C, 76.74; H, 7.80; N, 4.71. Found: C, 76.92; H, 7.86; N, 4.80.

EXAMPLE 25

Trans-4-(2,3-dimethylphenoxy)-3-pyrrolidinol Hydrobromide

A solution of 9.1 g. (0.031 mole) of trans-4-(2,3-dimethylphenoxy)-1-phenylmethyl-3-pyrrolidinol in 100 liters of ethanol was hydrogenated over 10% palladium-on-charcoal at 50 psi and 60° C. until hydrogen uptake ceased. The mixture was filtered through Celite and the filtrate was concentrated to give an oil as residue which solidified upon standing. The solid was converted to the hydrobromide and this salt was recrystallized from isopropyl alcohol-ethylacetate-diethylether to yield 4.9 g (55%) of tan needles, m.p. 152°-3° C.

Analysis: Calculated for $C_{12}H_{18}BrNO_2$: C, 50.01; H, 6.30; N, 4.86. Found: C, 50.29; H, 6.42; N, 4.85.

EXAMPLE 26

Trans-4-(2-methoxyphenoxy)-1-phenylmethyl-3-pyrrolidinol

A mixture of 40 g. of crude 1-benzyl-3,4-epoxypyrrolidine and 70 g. of guaiacol was heated at 120° C. for 20 hr. Aspirator vacuum was then used to distill off the excess guaiacol. The residue was dissolved in methylene chloride and extracted with dilute sodium hydroxide. The methylene chloride solution was dried over anhydrous sodium sulfate and the solvent was evaporated. The residue weighed 54 g., was chromatographed on 1 kg. of silica gel. The product was eluted with 50% ethyl acetate in benzene and crystallized from cyclohexane. The m.p. was 115°-117° C. and the yield was 27%.

Analysis: Calculated for $C_{18}H_{21}NO_3$: C, 72.22; H, 7.07; N, 4.68. Found: C, 72.30; H, 7.04; N, 4.70.

EXAMPLE 27

Trans-4-(2-methoxyphenoxy)-3-pyrrolidinol Fumarate

A solution of 11.5 g. of 1-benzyl-4-(o-methoxyphenoxy)-3-pyrrolidinol in 200 ml. of ethanol was treated with ca. 2 g. of 10% palladium-on-charcoal catalyst and was shaken with hydrogen at 60° C. in the Parr reduction apparatus for 5 hr. The suspension was then cooled, filtered, and the solvent evaporated at reduced pressure. The base was converted to the fumarate which melted at 158°-160° C. Yield was 9.8 g. (78%).

Analysis: Calculated for $C_{15}H_{19}NO_7$: C, 55.38; H, 5.89; N, 4.31. Found: C, 55.38; H, 5.89; N, 4.13.

EXAMPLE 28

Trans-4-(4-methoxyphenoxy)-1-phenylmethyl-3-pyrrolidinol

A mixture of 17.5 g. (0.10 mole) of 1-benzyl-3,4-epoxypyrrolidine, 13.4 g. (0.11 mole) of p-methoxyphenol, and 3 drops of water was heated on a steam bath overnight. The dark residue was dissolved in methylene chloride and the solution was washed with two 50-ml. portions of 5% sodium hydroxide. The methylene chloride layer was dried over anhydrous sodium sulfate and concentrated to give 23.7 g. of viscous dark oil. This oil was chromatographed on 480 g. of silica gel 60 and the product was eluted with a 1:1 benzene:ether solution. The appropriate fractions were concentrated to give 10.0 g. of a yellow oil which crystallized upon scratching. The solid was recrystallized from cyclohexane to yield 7.2 g. (24%) tan solid, m.p. 84°–5° C.

Analysis: Calculated for $C_{18}H_{21}NO_3$: C, 72.22; H, 7.07; N, 4.68. Found: C, 72.20; H, 7.15; N, 4.61.

EXAMPLE 29

Trans-4-(4-methoxyphenoxy)-3-pyrrolidinol Oxalate (3:4)

A solution of 4.0 g. (0.0134 mole) of trans-4-(4-methoxyphenoxy)-1-phenylmethyl-3-pyrrolidinol in 75 liters of ethanol was hydrogenated over 0.4 g. of 10% Pd/C at 60° C. overnight. The reaction mixture was cooled, filtered through Celite, and the filtrate concentrated to give the base as a white solid. This solid was converted to the oxalate and recrystallized from methanol to yield white flakes, m.p. 173°–175° C.d.

Analysis: Calculated for $C_{41}H_{53}N_3O_{25}$: C, 52.40; H, 5.68; N, 4.47. Found: C, 52.17; H, 5.62; N, 4.66.

EXAMPLE 30

Trans-4-(2-ethoxyphenoxy)-1-phenylmethyl-3-pyrrolidinol

A mixture of 45.5 g. (0.26 mole) of 1-benzyl-3,4-epoxypyrrolidine (60 g. of 76% epoxide), 48 g. (0.35 mole) of o-ethoxyphenol and 8 drops of concentrated hydrochloric acid was heated at 145° C. for 16 hr. The mixture was cooled, dissolved in methylene chloride and washed with dilute sodium hydroxide solution. The methylene chloride layer was dried over anhydrous sodium sulfate and the solvent was removed under reduced pressure. The residue was chromatographed on 1 kg. of silica gel using 20% acetone in benzene as the eluent. Two recrystallizations from cyclohexane gave 8.0 g. (10%) of tan needles, m.p. 88.5°–90.0° C.

Analysis: Calculated for $C_{19}H_{23}NO_3$: C, 72.82; H, 7.40; N, 4.47. Found: C, 72.64; H, 7.39; N, 4.56.

EXAMPLE 31

Trans-4-(2-ethoxyphenoxy)-3-pyrrolidinol Fumarate

A solution of 7.4 g. (24 mmoles) of trans-4-(2-ethoxyphenoxy)-1-phenylmethyl-3-pyrrolidinol in 150 ml. of absolute ethanol was treated with about 0.5 g. of 10% Pd/C catalyst and was shaken with hydrogen in the Parr reduction apparatus at 60° C. for 1.5 hr. The mixture was cooled and filtered and the filtrate was concentrated. The residue (5.3 g., 100%) was converted to the fumarate in isopropyl alcohol to give a white powder; m.p. 173.0°–174.5° C.

Analysis: Calculated for $C_{16}H_{21}NO_7$: C, 56.63; H, 6.24; N, 4.13. Found: C, 56.60; H, 6.27; N, 4.12.

EXAMPLE 32

Trans-4-[4-(phenylmethoxy)phenoxy]-1-phenylmethyl-3-pyrrolidinol

A mixture of 40 g. of 1-benzyl-3,4-epoxypyrrolidine and 42 g. of 4-benzoxyphenol was heated at 130° C. for 8 hr. On cooling, the mixture crystallized. Three crystallizations from petroleum ether-cyclohexane gave fluffy white crystals melting at 98.0°–100.0° C. The yield was 6.0 g. (8%).

Analysis: Calculated for $C_{24}H_{25}NO_3$: C, 76.78; H, 6.71; N, 3.73. Found: C, 76.83; H, 6.82; N, 3.57.

EXAMPLE 33

Trans-4-(4-hydroxyphenoxy)-3-pyrrolidinol Hemioxalate

Six grams of 1-benzyl-4-(4-benzoxyphenoxy)-3-pyrrolidinol in 150 ml. of ethanol was treated with ca. 1 g. of palladium-on-charcoal and shaken under hydrogen at 60° C. in the Parr apparatus for 3 hr. The mixture was then cooled, filtered and the ethanol removed. The oxalate was made in isopropyl alcohol acetone and recrystallized from 90% ethanol. The salt decomposed at 235° C.

Analysis: Calculated for $C_{11}H_{14}NO_5$: C, 55.00; H, 5.87; N, 5.83. Found: C, 54.54; H, 5.83; N, 5.65.

EXAMPLE 34

Trans-4-(3-trifluoromethylphenoxy)-1-phenylmethyl-3-pyrrolidinol Oxalate

A mixture of 24.0 g. of 1-benzyl-3,4-epoxypyrrolidine and 22.2 g. of 3-trifluoromethylphenol was heated at 130° C. for 3 hr. The mixture was cooled, dissolved in methylene chloride and extracted with dilute sodium hydroxide. The residue after the solvent was evaporated was purified by column chromatography. The product, which was eluted using 30% ethyl acetate in benzene weighed 17.7 g. (38%). A small portion when converted to the oxalate melted at 139°–141° C.

Analysis: Calculated for $C_{20}H_{20}NO_6F_3$: C, 56.21; H, 4.72; N, 3.28. Found: C, 56.48; H, 4.77; N, 3.44.

EXAMPLE 35

Trans-4-(3-trifluoromethylphenoxy)-3-pyrrolidinol Hydrochloride

A solution of 12.6 g. of trans-1-benzyl-4-(3-trifluoromethylphenoxy)-3-pyrrolidinol in 200 ml. of ethanol was treated with ca. 2 g. of 10% palladium-on-charcoal catalyst and was shaken with hydrogen at 60° C. in the Parr reduction apparatus for 16 hr. The suspension was cooled, filtered and the solvent evaporated at reduced pressure. The residue was dissolved in ether and converted to the hydrochloride. The yield of product melting at 145°–8° C. was 9.8 g. (93%).

Analysis: Calculated for $C_{11}H_{13}NO_2ClF_3$: C, 46.58; H, 4.62; N, 4.94. Found: C, 46.42; H, 4.68; N, 5.07.

EXAMPLE 36

Trans-4-[(4-hydroxy-1-phenylmethyl-pyrrolidin-3-yl)oxy]benzamide

A mixture of 28 g. of 1-benzyl-3,4-epoxypyrrolidine and 20.6 g. of 4-hydroxybenzamide was heated at 130° C. for 8 hrs. The cooled mixture was columned on silica gel using 5% methanol in ethyl acetate to elute the product, which was then crystallized from chloroform-benzene-methanol. The yield was 19% of product melting at 133.0°–6.0° C.

Analysis: Calculated for $C_{18}H_{20}N_2O_3$: C, 69.21; H, 6.45; N, 8.97. Found: C, 69.11; H, 6.46; N, 8.82.

EXAMPLE 37

Trans-4-[(4-hydroxy-3-pyrrolidinyl)oxy]benzamide

Eight grams of 4-[(4-benzamide)oxy]-1-benzyl-3-pyrrolidinol was treated with ca. 1 g. of 10% palladium-on-charcoal and dissolved in 100 ml. of ethanol and shaken with hydrogen at 60° C. for 4 hr. The suspension was then cooled and filtered. The precipitate was washed with hot methanol and the washings combined with the mother liquor. The solvent was evaporated to 150 ml. and cooled overnight. The product was filtered and dried and melted at 199°–204° C. with decomposition. The yield was 80%.

Analysis: Calculated for $C_{11}H_{14}N_2O_3$: C, 59.45; H, 6.35; N, 12.61. Found: C, 59.47; H, 6.45; N, 12.57.

EXAMPLE 38

Trans-N-{4-[(4-hydroxy-1-phenylmethyl-3-pyrrolidinly)oxy]phenyl}acetamide

A mixture of 35.0 g. of 1-benzyl-3,4-epoxypyrrolidine, 30.2 g. of p-acetamidophenol and two drops of water was heated at 125° C. for 3 hr. The mixture was then cooled, dissolved in 50% ethyl acetate in benzene and washed with dilute sodium hydroxide. When the solvent was removed, the residue weighed 56 g. It was chromatographed using 370 g. of silica gel and the product was eluted with ethyl acetate. After crystallization from 50% ethyl acetate in benzene, the product melted at 130°–32° C. and weighed 26.1 g. (40%).

Analysis: Calculated for $C_{19}H_{22}N_2O_3$: C, 69.92; H, 6.79; N, 8.58; O, 14.7. Found: C, 69.61; H, 6.69; N, 8.44.

EXAMPLE 39

Trans-N-{4-[(4-hydroxy-3-pyrrolidinyl)oxy]phenyl-}acetamide Hemifumarate

A solution of 12.4 g. of 1-benzyl-4-(4-acetamidophenoxy)-3-pyrrolidinol in 200 ml. of ethanol was treated with ca. 2 g. of 10% palladium-on-charcoal catalyst and was shaken with hydrogen at 60° C. in the Parr reduction apparatus for 16 hr. The suspension was then cooled, filtered and the solvent evaporated at reduced pressure. The residue weighed 9 g. and was converted to the fumarate and crystallized from isopropyl alcohol. The yield of salt was 10.2 g. (90%) which melted at 200°–05° C.

Analysis: Calculated for $C_{14}H_{19}N_2O_5$: C, 57.14; H, 6.17; N, 9.52. Found: C, 56.90; H, 6.22; N, 9.29.

Example 40

Trans-4-(1-naphthalenyloxy)-1-phenylmethyl-3-pyrrolidinol Oxalate

A mixture of 17.5 g. (0.10 mole) of crude 1-benzyl-3,4-epoxypyrrolidine, 15.0 g. (0.11 mole) of 1-naphthol and 1 drop of concentrated hydrochloric acid was heated on a steam bath overnight. The dark mixture was dissolved in methylene chloride and the solution was extracted with three 50 ml. portions of 5% sodium hydroxide. The methylene chloride layer was dried over anhydrous sodium sulfate and concentrated to give 25.5 g. (80%) of black gum as residue. This residue was chromatographed on 500 g. of silica gel and the product was eluted with 1:1 ethyl ether;benzene to give 9.9 g. (31%) of white solid, m.p. 106–8° C. when recrystallized from cyclohexane.

Analysis: Calculated for $C_{21}H_{21}NO_2$: C, 79.97; H, 6.63; N, 4.39. Found: C, 79.08; H, 6.67; N, 4.45.

The oxalate was prepared as a white solid, m.p. 190–2° C. when recrystallized from nitromethane.

Analysis: Calculated for $C_{23}H_{23}NO_6$: C, 67.47; H, 5.66; N, 3.42. Found: C, 67.00; H, 5.68; N, 3.57.

Example 41

Trans-4-(1-naphthalenyloxy)-3-pyrrolidinol

Eighteen grams of 1-benzyl-4-(1-naphthoxy)-3-pyrrolidinol in 200 ml. of ethanol was treated with ca. 2 g. of 10% palladium-on-charcoal under hydrogen at 60° C. for 20 hr. The mixture was cooled, filtered and ethanol removed. The residue was crystallized from benzene and had a melting point of 112°–115° C.

Analysis: Calculated for $C_{14}H_{15}NO_2$: C, 73.34; H, 6.59; N, 6.11. Found: C, 73.39; H, 6.64; N, 5.90.

Example 42

Trans-4-[1H-2,3-dihydroinden-4-yl)oxy]-1-phenylmethyl-3-pyrrolidinol

A mixture of 28 g. of 1-benzyl-3,4-epoxypyrrolidine and 20.1 g. of 4-indanol was heated at 130° C. for 8 hr. The residue was chromatographed on silica gel using ethyl acetate to elute the product. The yield of product after crystallization from cyclohexane was 6%, melting at 98°–101° C.

Analysis: Calculated for $C_{20}H_{23}NO_2$: C, 77.64; H, 7.49; N, 4.53. Found: C, 77.41; H, 7.52; N, 4.37.

Example 43

Trans-4-[1H-2,3-dihydroinden-4-yl)oxy]-3-pyrrolidinol Hydrochloride

1-Benzyl-4-(4-indanoxy)-3-pyrrolidinol (2.7 g.) in 100 ml. of ethanol treated with ca. 0.5 g. 10% palladium-on-charcoal and was shaken with hydrogen at 60° C. in the Parr apparatus for 5 hr. The suspension was then cooled, filtered and the solvent removed. The residue was converted to the hydrochloride in ether and dried for 18 hr. at 40° C. under vacuum. The yield of product melting at 174°–180° C. was 91%.

Analysis: Calculated for $C_{13}H_{16}NO_2Cl$: C, 61.06; H, 7.09; N, 5.48. Found: C, 60.80; H, 7.16; N, 5.46.

Example 44

Trans-4-[(1,2-dihydroinden-5yl)oxy]-1-phenylmethyl-3-pyrrolidinol Hydrochloride

A mixture of 35 g. of 1-benzyl-3,4-epoxypyrrolidine and 28 g. of 5-indanol was heated at 130° C. for 3 hr. The mixture was then cooled, dissolved in methylene chloride and extracted with dilute sodium hydroxide. After solvent evaporation the residue was columned on silica gel, and the product was eluted with 50% ethyl acetate in benzene. The hydrochloride salt was formed in ether and was recrystallized from ethanol-acetone. The yield of salt melting at 153–5° C. was 12.3 g. (18%).

Analysis: Calculated for $C_{20}H_{24}NO_2Cl$: C, 69.45; H, 6.99; N, 4.05. Found: C, 69.13; H, 6.93; N, 3.99.

Example 45

Trans-4[(2,3-dihydro-1H-inden-5-yl)oxy]-3-pyrrolidinol Oxalate

A solution of 6.0 g. of 1-benzyl-4-(5-indanoxy-3-pyrrolidinol in 100 ml. of ethanol was treated with ca. 0.5 g. 10% palladium-on-charcoal and was shaken with hydrogen at 60° C. in the Parr apparatus for 3 hr. The suspension was then cooled, filtered, and the solvent removed. The oxalate was prepared in isopropyl alcohol and melted at 179.0°–181.0° C.

Analysis: Calculated for $C_{15}H_{19}NO_6$: C, 58.25; H, 6.19; N, 4.53. Found: C, 58.13; H, 6.14; N, 4.58.

Example 46

Trans-1-ethyl-4-phenoxy-3-pyrrolidinol Oxalate Hydrate (4:1)

A mixture of 22.6 g. of 1-ethyl-3,4-epoxypyrrolidine and 18.6 g. of phenol was heated at 150° C. for 0.5 hr., and then distilled. The product boiled at 120°/0.025 mm. The yield of pure product was 25.0 g. (60%). A portion of the base was converted to the oxalate which melted at 134–7° C. after it was recrystallized from isopropyl alcohol.

Analysis: Calculated for $C_{56}H_{78}N_4O_{25}$: C, 55.72; H, 6.51; N, 4.64. Found: C, 55.83; H, 6.38; N, 4.63.

Example 47

Trans-1-ethyl-4-phenoxy-3-pyrrolidinolmethylcarbamate Ester

A solution of 6.5 g. of 1-ethyl-4-phenoxy-3-pyrrolidinol and 1.9 g. of methyl isocyanate in 80 ml. of benzene was allowed to stand under nitrogen gas for 5 days. The crystalline solid remaining on evaporation of the benzene was recrystallized from cyclohexane. The yield of product melting at 88°–94° C. was 6.5 g. (79%).

Analysis: Calculated for $C_{14}H_{20}N_2O_3$: C, 63.62; H, 7.63; N, 10.60. Found: C, 63,61; H, 7.60; N, 10.62.

Example 48

Trans-4-(2-chlorophenoxy)-1-ethyl-3-pyrrolidinol Hydrochloride

A mixture of 17.0 g. (0.15 mole) of 1-ethyl-3,4-epoxypyrrolidine, 20.5 g. (0.16 mole) of o-chlorophenol and 3 drops concentrated hydrochloric acid was heated on a steam both overnight. The oil was dissolved in methylene chloride and washed with three 50-ml. portions of 5% sodium hydroxide and one 50-ml. portion of water. The methylene chloride solution was dried over anhydrous sodium sulfate, concentrated and chromatographed on silica gel to give 8.9 g. (25%) of an oil as residue. The oil was converted to the hydrochloride and recrystallized from ethyl acetate-acetonitrile to yield white powder, m.p. 108°–110° C.

Analysis: Calculated for $C_{12}H_{17}Cl_2NO_2$: C, 51.81; H, 6.16; N, 5.04. Found: C, 51.65; H, 6.17; N, 5.09.

Example 49

Trans-4-(2,6-dichlorophenoxy)-1-ethyl-3-pyrrolidinol Hydrochloride

A mixture of 11.3 g. (0.10 mole) of 1-ethyl-3,4-epoxypyrrolidine, 18.0 g. (0.11 mole) of 2,6-dichlorophenol and 2 drops concentrated hydrochloric acid was heated on a steam bath overnight. The oil was dissolved in methylene chloride and washed with three 50-ml. portions of 5% sodium hydroxide and one 50-ml. portion of water. The methylene chloride solution was dried over anhydrous sodium sulfate, concentrated and chromatographed on silica gel to give 12.9 g. (47%) of an oil residue. The oil was converted to the hydrochloride ad recrystallized from isopropyl alcohol-diethyl ether to yield 12.3 g. (39%), m.p. 160°–162° C.

Analysis: Calculated for $C_{12}H_{16}Cl_3NO_2$: C, 46.10; H, 5.16; N, 4.48. Found: C, 46.10; H, 5.20; N, 4.48.

Example 50

Trans-1-ethyl-4-(3-methylphenoxy)-3-pyrrolidinol Oxalate Hemihydrate

A mixture of 17 g. of 1-ethyl-3,4-epoxypyrrolidine and 16.2 g. of m-cresol was heated at 125° C. for 45 min. and then vacuum distilled. The yield of product boiling at 135° C./0.02 mm was 37%. This was converted to the oxalate which melted at 116°–119° C.

Analysis: Calculated for $C_{30}H_{44}N_2O_{13}$: C, 56.24; H, 6.92; N, 4.37. Found: C, 56.66; H, 6.68; N, 4.15.

Example 51

Trans-4-(2-ethoxyphenoxy)-1-ethyl-3-pyrrolidinol

A mixture of 17.0 g. (0.15 mole) of 1-ethyl-3,4-epoxypyrrolidine, 22.1 g. (0.16 mole) of o-ethoxyphenol and 3 drops of concentrated hydrochloric acid was heated on a steam bath overnight. The oil was dissolved in methylene chloride and washed with three 50-ml. portions of 5% sodium hydroxide and one 50-ml. portion of water. The methylene chloride solution was dried over anhydrous sodium sulfate, concentrated and chromatographed on silica gel to give 8.1 g. (21%) of an oil which crystallized on standing. The solid was recrystallized from cyclohexane to yield a tan solid, m.p. 73°–75° C.

Analysis: Calculated for $C_{14}H_{21}NO_3$: C, 66.90; H, 8.42; N, 5.57; Found: C, 66.49; H, 8.43; N, 5.48.

Example 52

Trans-1-{4-[(1-ethyl-4-hydroxy-3-pyrrolidinyl)oxy]-3-methoxyphenyl}ethanone Sesquioxalate A mixture of 17.0 g. (0.15 mole) of acetovanillone and 1-ethyl-3,4-epoxypyrrolidine and 3 drops of water was heated on a steam bath overnight. The mixture was dissolved in 250 ml. of methylene chloride and extracted with three 150-ml. portions of 5% sodium hydroxide and one 100-ml. portion of water. The methylene chloride layer was dried over anhydrous sodium sulfate and concentrated to give 19.0 g. crude oil. This oil was chromatographed on 400 g. of silica gel. The desired product was eluted with acetone. The fractions were concentrated to give 14.0 g. of oil which was treated with oxalic acid in isopropyl alcohol. The resulting white solid was recrystallized twice from isopropyl alcohol to yield 13.4 g. (24%) of sesquioxalate, m.p. 121–3° C.

Analysis: Calculated for $C_{16}H_{24}NO_{10}$: C, 52.17; H, 5.84; N, 3.38. Found: C, 52.45; H, 5.90; N, 3.60.

Example 53

Trans-1-ethyl-4-[2-(2-propenyl)phenoxy]-3-pyrrolidinol Oxalate

A mixture of 17.0 g. of 1-ethyl-3,4-epoxypyrrolidine and 20.0 g. of 2-allylphenol was heated at 130° C. for 1.5 hr. then cooled and chromatographed on silica gel, using 20% methanol in ethyl acetate to elute the product. A portion of the total yield, 18.5 g. (50%) was converted to the oxalate which melted at 142–5° C.

Analysis: Calculated for $C_{17}H_{23}NO_6$: C, 60.52; H, 6.87; N, 4.15. Found: C, 60.30; H, 6.79; N, 3.98.

Example 54

Trans-1-ethyl-4-[2-(2-propenyl)phenoxy]-3-pyrrolidinol ethylcarbamate (ester)

A mixture of 7.3 g. of trans 4-(2-allylphenoxy)-1-ethyl-3-pyrrolidinol and 2.5 g. of ethylisocyanate in 30 ml. of benzene was stirred for 48 hr. The benzene was replaced by petroleum ether and the solution chilled. The yield of precipitate melting at 53–6° C. was 78%.

Analysis: Calculated for $C_{18}H_{26}N_2O_3$: C, 67.90; H, 8.23; N, 8.80. Found: C, 67.91; H, 8.08; N, 8.79.

Example 55

Trans-1-ethyl-4-(1-naphthalenyloxy)-3-pyrrolidinol Hydrochloride

A mixture of 22.6 g. of 3,4-epoxy-1-ethylpyrrolidine and 28.8 g. of 1-naphthol was heated to 130° C. for 1 hr.

The mixture was cooled, dissolved in benzene and extracted with dilute sodium hydroxide. The benzene was evaporated and the residue was chromatographed on silica gel, eluting the product with 40% methanol in ethyl acetate. The hydrochloride of the product was made and recrystallized from ethanol-acetone. The yield of salt melting at 206-7° C. was 17.5 g. (30%).

Analysis: Calculated for $C_{16}H_{20}NO_2Cl$: C, 65.41; H, 6.86; N, 4.77. Found: C, 65.29; H, 6.93; N, 4.70.

Example 56

Trans-1-ethyl-4-[(1H-2,3-dihydroinden-4-yl)oxy]-3-pyrrolidinol

A mixture of 17 g. of 1-ethyl-3,4-epoxypyrrolidine and 20 g. of 4-indanol was heated at 125° C. for 1 hr. then cooled and dissolved in ethyl acetate and chromatographed on silica gel, using 25% methanol in ethyl acetate to elute the product. The yield of product melting at 87°-90° C. after recrystallization from cyclohexane was 15 g. (40%).

Analysis: Calculated for $C_{15}H_{21}NC_2$: C, 72.84; H, 8.56; N, 5.66. Found: C, 72.92; H, 8.52; N, 5.48.

Example 57

Trans-1-ethyl-4-[(1H-2,3-dihydroinden-5-yl)oxy]-3-pyrrolidinol Maleate

A mixture of 15.0 g. (0.132 mole) of 1-ethyl-3,4-epoxypyrrolidine, 20 g. (0.15 mole) of 5-indanol and 1 drop of water was heated on a steam bath overnight. The oil eas dissolved in methylene chloride and washed with three 50-ml. portions of 5% sodium hydroxide and one 50-ml. portion of water. The methylene chloride was dried over anhydrous sodium sulfate and concentrated to give 28.5 g. of a dark residue. This residue was chromatographed on 500 g. of silica gel and the product was eluted with methanol. This oil was converted to the maleate to yield 16.6 g. (35%) of cream colored needles, m.p. 147-8° C.

Analysis: Calculated for $C_{19}H_{25}NO_6$: C, 62.80; H, 6.93; N, 3.85. Found: C, 62.74; H, 6.88; N, 3.83.

Example 58

Trans-1-cyclohexyl-4-phenoxy-3-pyrrolidinol Compound with Cyclohexane-sulfamic Acid A mixture of 33.5 g. (0.2 mole) of N-cyclohexyl-3,4-epoxypyrrolidine, 18.8 g. (0.02 mole) of phenol and 2 drops concentrated hydrochloric acid was heated on a steam bath overnight. The reaction mixture was dissolved in methylene chloride and washed with three 100-ml portions of 5% sodium hydroxide and once with 100 ml. of water and dried over potassium hydroxide-anhydrous sodium sulfate. The methylene chloride solution was concentrated to give 36.4 g. of oil as residue. The oil partially crystallized and the solid was washed with petroleum ether, collected by filtration and recrystallized from cyclohexane to give 11.0 g. (21%) of a white solid. This solid was converted to the hexamate to yield white needles, m.p. 163-5° C., recrystallized from isopropyl alcohol.

Analysis: Calculated for $C_{22}H_{36}N_2O_5S$: C, 59.97; H, 8.24 N, 6.36. Found: C, 59.99; H, 8.29; N, 6.30.

Example 59

Cis-4-phenoxy-1-phenylmethyl-3-pyrrolidinol

A slurry of 2.4 g. (0.1 mole) of sodium hydride (4.2 g. of 57% oil dispersion, washed with ether to remove the oil) in 30 ml. of dimethylformamide was stirred while a solution of 19.3 g. (0.1 mole) of 1-benzyl-3,4-dihydroxypyrrolidine, cis isomer, (I) in 30 ml. of dimethylformamide was added dropwise. The mixture was heated at 50° C. for 1 hr., then a solution of 19.2 g. (0.2 mole) of fluorobenzene in 30 ml. of dimethylformamide was added in one portion. The mixture was heated at 90° C. for 18 hr., then cooled and concentrated under vacuum. The residue was dissolved in benzene and washed with water. The semicrystalline residue from the concentrated organic fraction was dissolved in cyclohexane and the solution was decanted from an insoluble oil (mostly I). The cyclohexane solution was treated with charcoal to remove residual I and then crystallized as fluffy, off-white needles (m.p. 88.5°-90° d.) which weighed 1.2 g. (4.5%).

Analysis: Calculated for $C_{17}H_{19}NO_2$: C, 75.81; H, 7.11; N, 5.20. Found: C, 75.88; H, 7.27; N, 5.16.

Example 60

Cis-4-(3-chlorophenoxy)-1-phenylmethyl-3-pyrrolidinol

A slurry of 1.2 g. (50 mmoles) of sodium hydride (2.1 g. of 57% oil dispersion, washed with ether to remove the oil) in 25 ml. of dimethyl sulfoxide was stirred while 9.6 g. (50 mmoles) of 1-benzyl-3,4-dihydroxypyrrolidine, cis isomer, in 25 ml. of dimethyl sulfoxide was added. The mixture was stirred at ambient temperature for one hr., then 50 ml. of dimethyl sulfoxide was added and the temperature was raised to 95° C. for 0.5 hr. Mechanical stirring of the thick slurry was necessary while 13 g. (100 mmoles) of m-chlorofluorobenzene was added. During the heating period of 1 hr. at 95° C., all precipitate dissolved. The reaction mixture was concentrated by vacuum distillation of the dimethyl sulfoxide and excess m-chlorofluorobenzene. The residue was poured into water and extracted with hot cyclohexane. The organic extracts were combined, dried over anhydrous sodium sulfate and concentrated to give 7.5 g. (49%) of off-white crystals, m.p. 86°-87.5° C.

Analysis: Calculated for $C_{17}H_{18}ClNO_2$: C, 67.21; H, 5.97; N, 4.61. Found: C, 67.33; H, 6.00; N, 4.56.

Example 61

Cis-3-(3-chlorophenoxy)-4-hydroxy-1-methyl-1-phenylmethylpyrrolidinium Iodide

A mixture of 15.2 g. (0.05 mole) of cis-4-(3-chlorophenoxy)-1-phenylmethyl-3-pyrrolidinol and 56 g. (0.4 mole) of methyl iodide was heated at reflux for 60 hr. Excess methyl iodide was removed under vacuum. The pasty residue was washed with ether-acetone, leaving 13 g. (59%) of granular tan powder, m.p. 118-25° C.

Analysis: Calculated for $C_{18}H_{21}ClINO_2$: C, 48.51; H, 7.75; N, 3.14. Found: C, 48.27; H, 4.75; N, 3.19.

Example 62

Cis-1-methyl-4-phenoxy-3-pyrrolidinol

A solution of 12.5 g. (28 mmoles) of cis-3-(3-chlorophenoxy)-4-hydroxy-1-methyl-1-phenylmethylpyrrolidinium iodide in 400 ml. of ethanol was stirred at 45° C. with 3.5 g. (15 mmoles) of silver oxide for 1 hr. The solids were removed by filtration and the filtrate was concentrated to 100 ml., treated with 0.5 g. of 10% palladium-on-charcoal catalyst and was shaken under hydrogen at 60° C. for 3 hr. The mixture was cooled and the catalyst was collected by filtration. The filtrate was concentrated and the residue was treated with dilute sodium hydroxide and extracted into methylene chloride. The solution was concentrated and redissolved in hot cyclohexane, treated with charcoal, separated by filtration through Celite and recrystallized from cyclohexane to give 4.6 g. (85%) of white needles (m.p. 78°–81° C.).

Analysis: Calculated for $C_{11}H_{15}NO_2$: C, 68.37; H, 7.82; N, 7.25. Found: C, 68.42; H, 7.87; N, 7.19.

Example 63

Cis-4-phenoxy-3-pyrrolidinol cis isomer Hydrochloride Hydrate (4:1)

A solution of 16.0 g. (53 mmoles) of cis-4-(3-chlorophenoxy)-1-phenylmethyl-3-pyrrolidinol in 100 ml. of absolute ethanol and 5 ml. concentrated hydrochloric acid was treated with 0.5 g. of 10% palladium-on-charcoal catalyst and was shaken under hydrogen at 60° C. for 16 hr. The mixture was cooled and the catalyst was separated by filtration through Celite. The filtrate was concentrated and the white crystalline residue was triturated with ether-acetone. Weight of white powder, 9.8 g. (86%), m.p. 128–37° C. was obtained.

Analysis: Calculated for $C_{40}H_{58}Cl_4N_4O_9$: C, 54.55; H, 6.64; N, 6.36. Found: C, 54.26; H, 6.41; N, 6.27.

Formulation and Administration

Effective quantities of any of the foregoing pharmacologically active compounds of Formula I may be administered to a living animal body for therapeutic purposes according to usual modes of administration and in usual forms, such as orally in solutions, emulsions, suspensions, pills, tablets and capsules in pharmaceutically acceptable carriers and parenterally in the form of sterile solutions.

For the parenteral administration the carrier or excipient may be a sterile, parenterally acceptable liquid; e.g., water or a parenterally acceptable oil; e.g., arachis oil contained in ampules.

Although very small quantities of the active materials of the present invention are effective when minor therapy is involved or in cases of administration to subjects having a relatively low body weight, unit dosages are usually from five milligrams or above and preferably 25, 50, or 100 milligrams or even higher, depending, of course, upon the emergency of the situation and the particular result desired. Five to 50 milligrams appears optimum per unit dose or usual broader ranges appear to be 1 to 500 milligrams per unit dose. Daily dosages should preferably range from 10 mg. to 100 mg. The active ingredients of the invention may be combined with other pharmacologically active agents as stated above. It is only necessary that the active ingredient constitute an effective amount, i.e., such that a suitable effective dosage will be obtained consistent with the dosage form employed. Obviously, several unit dosage forms may be administered at about the same time. The exact individual dosages as well as daily dosages will, of course, be determined according to standard medical principles under the direction of a physician or veterinarian.

The following formulations are representative for all of the pharmacologically active compounds of this invention. cl FORMULATIONS 1. Capsules Capsules of 5 mg., 10 mg., 25 mg., and 50 mg. of active ingredient per capsule are prepared. With the higher amounts of active ingredient, reduction may be made in the amount of lactose.

| Typical blend for encapsulation | Per Capsule, mg. |
| --- | --- |
| Active ingredient, as salt | 5 |
| Lactose | 259 |
| Starch | 126 |
| Magnesium stearate | 4 |
| Total | 394 |

Additional capsule formulations preferably contain a higher dosage of active ingredient and are as follows:

| Ingredients | 100 mg. per Capsule | 250 mg. per Capsule | 500 mg. per Capsule |
| --- | --- | --- | --- |
| Active ingredient, as salt | 100 | 250 | 500 |
| Lactose | 214 | 163 | 95 |
| Starch | 87 | 81 | 47 |
| Magnesium stearate | 4 | 6 | 8 |
| Total | 399 | 500 | 650 |

In each case, uniformly blend the selected active ingredient with lactose, starch, and magnesium stearate and encapsulate the blend.

2. Tablets

A typical formulation for a tablet containing 5.0 mg. of active ingredient per tablet follows. The formulation may be used for other strengths of active ingredient by adjustment of weight of dicalcium phosphate.

| | | Per Tablet, mg. |
| --- | --- | --- |
| 1. | Active ingredient | 5.0 |
| 2. | Corn starch | 15.0 |
| 3. | Corn starch (paste) | 12.0 |
| 4. | Lactose | 35.0 |
| 5. | Dicalcium phosphate | 132.0 |
| 6. | Calcium stearate | 2.0 |
| | Total | 202.0 |

Uniformly blend 1, 2, 4 and 5. Prepare 3 as a 10 percent paste in water. Granulate the blend with starch paste and pass the wet mass through an 8 mesh screen. The wet granulation is dried and sized through a 12 mesh screen. The dried granules are blended with the calcium stearate and compressed.

| 3. Injectable - 2% sterile solution | Per cc |
| --- | --- |
| Active ingredient    mg. | 20 |
| Preservative, e.g. chlorobutanol, wt./vol. percent | 0.5 |
| Water for injection q.s. | |

Prepare solution, clarify by filtration, fill into vials, seal and autoclave.

Various modifications and equivalents will be apparent to one skilled in the art and may be made in the compounds, compositions and methods of the present invention without departing from the spirit or scope thereof, and it is therefore understood that the invention is to be limited only by the scope of the appended claims.

What is claimed:

1. A method of treating depression in animals which comprises administering to said animal an effective amount of a trans-4-(2-chlorophenoxy)-1-ethyl-3-pyrrolidinol and the pharmaceutically acceptable acid addition salts thereof.

2. Trans-4-(2-chlorophenoxy)-1-ethyl-3-pyrrolidinol and the pharmaceutically acceptable addition salts thereof.

3. A pharmaceutical composition comprising trans-4-(2-chlorophenoxy)-1-ethyl-3-pyrrolidinol and the pharmaceutically acceptable addition salts thereof and a pharmaceutical carrier therefor.

* * * * *

UNITED STATES PATENT OFFICE
CERTIFICATE OF CORRECTION

Patent No. 4,452,809                    Dated  June 5, 1984

Inventor(s)  David A. Walsh and William J. Welstead, Jr.

It is certified that error appears in the above-identified patent and that said Letters Patent are hereby corrected as shown below:

Col. 1, line 58, add a parenthesis after "2".

Col. 2, line 35, "barbiturate" should be --barbituate--.

Col. 2, line 68, "antharrhythmic" should be --antiarrhythmic--.

Co. 3, line 34, insert a comma between "butyl" and "isobutyl".

Co. 4, line 20 "pyrrolines" should be --pyrrolidines--.

Col. 5, line 59, underline "meso".

Col. 19, Example 38, line 9-10 "pyrrolidinly" should be --pyrrolidinyl--.

Col. 19, Example 39, line 37, "$H_{19}$" should be --$H_{18}$--.

Col. 19, Example 40, line 53, delete ";" between "ether" and "benzene".

Col. 19, Example 40, line 56 "79.97" should be --78.97--.

Col. 21, Example 47, line 19, "C," should be --C.--.

UNITED STATES PATENT OFFICE
CERTIFICATE OF CORRECTION

Patent No. 4,452,809    Dated June 5, 1984

Inventor(s) David A. Walsh and William J. Welstead, Jr.

It is certified that error appears in the above-identified patent and that said Letters Patent are hereby corrected as shown below:

Col. 21, Example 48, line 28, "both" should be --bath--.

Col. 21, Example 49, line 52 "ad" should be --and--.

Col. 23, Example 56, line 21, "$NC_2$" should be --$NO_2$--.

Col. 23, Example 57, line 30, "eas" should be --was--.

Col. 24, Example 61, line 54 "7.75" should be --4.75--.

Col. 25, line 64, delete "Cl" and "FORMULATIONS" is a heading.

Col. 26, line 50, underline "Per cc".

Signed and Sealed this

Twentieth Day of November 1984

[SEAL]

Attest:

GERALD J. MOSSINGHOFF

Attesting Officer    Commissioner of Patents and Trademarks